United States Patent
Yaniv

(10) Patent No.: US 7,632,548 B2
(45) Date of Patent: Dec. 15, 2009

(54) REMOTE IDENTIFICATION OF EXPLOSIVES AND OTHER HARMFUL MATERIALS

(75) Inventor: Zvi Yaniv, Austin, TX (US)

(73) Assignee: Applied Nanotech Holdings, Inc., Austin, TX (US)

( * ) Notice: Subject to any disclaimer, the term of this patent is extended or adjusted under 35 U.S.C. 154(b) by 719 days.

(21) Appl. No.: 10/633,335

(22) Filed: Aug. 1, 2003

(65) Prior Publication Data

US 2004/0091635 A1    May 13, 2004

Related U.S. Application Data

(60) Provisional application No. 60/400,784, filed on Aug. 2, 2002.

(51) Int. Cl.
   *B05D 3/06*    (2006.01)
(52) U.S. Cl. .................................................. 427/558
(58) Field of Classification Search .................. 427/558
   See application file for complete search history.

(56) References Cited

U.S. PATENT DOCUMENTS

| | | | |
|---|---|---|---|
| 4,740,086 A | | 4/1988 | Oehler et al. |
| 5,457,073 A | * | 10/1995 | Ouellet ........................ 438/624 |
| 5,615,043 A | | 3/1997 | Plaessmann et al. |
| 5,990,479 A | * | 11/1999 | Weiss et al. .................. 250/307 |
| 6,261,779 B1 | * | 7/2001 | Barbera-Guillem et al. .... 435/6 |
| 6,380,550 B1 | | 4/2002 | Canham et al. |
| 6,458,327 B1 | * | 10/2002 | Vossmeyer .................. 422/68.1 |
| 6,530,944 B2 | * | 3/2003 | West et al. ...................... 607/88 |
| 6,537,755 B1 | | 3/2003 | Drmanac ......................... 435/6 |
| 6,544,732 B1 | * | 4/2003 | Chee et al. ....................... 435/6 |
| 6,692,031 B2 | * | 2/2004 | McGrew ........................ 283/93 |
| 6,778,165 B2 | * | 8/2004 | Hubby et al. ................ 345/107 |
| 6,797,944 B2 | | 9/2004 | Nguyen et al. |
| 6,908,737 B2 | * | 6/2005 | Ravkin et al. ................... 435/6 |
| 6,929,950 B2 | | 8/2005 | Canham et al. |
| 2002/0004246 A1 | * | 1/2002 | Daniels et al. ............... 436/514 |
| 2003/0013091 A1 | * | 1/2003 | Dimitrov ........................ 435/6 |
| 2004/0009911 A1 | * | 1/2004 | Harris et al. ................... 514/12 |
| 2004/0166319 A1 | | 8/2004 | Li et al. |

OTHER PUBLICATIONS

P. Przybylowicz et al., *Black and Smokeless Powders, Technologies for Finding Bombs and the Bomb Makers*, National Academy Press, Washington D.C. 1998, 164 pp.

(Continued)

*Primary Examiner*—Elena T Lightfoot
(74) *Attorney, Agent, or Firm*—Kelly Kordzik; Matheson Keys Garrson & Kordzik PLLC

(57) ABSTRACT

The present invention is for a process of sensing chemicals with nanoparticles, particularly nanoparticles whose bandgap has been altered from that of their corresponding bulk material by reducing their particle size below their quantum confinement threshold. The photoluminescent properties of these nanoparticles can be altered as a result of interaction with their chemical environment. Thus, by carefully understanding how a particular chemical species alters the chemical environment and changes the photoluminescence of the nanoparticles, the identification of—and the screening for—a wide range of chemical species can be accomplished. Furthermore, in embodiments in which the chemical species of interest is a harmful material, detection and screening of said harmful material can be carried out in a pre-emptive manner.

25 Claims, 1 Drawing Sheet

OTHER PUBLICATIONS

Anaple, G., et al., "Molecular structure of porous Si," *J. Appl. Phys.* 78(6), pp. 4273-4275. Sep. 15, 1995.

Heinrich, J., et al., "Luminescent Colloidal Silicon Suspensions from Porous Silicon," *Science*, vol. 255, pp. 66-68. Jan. 3, 1992.

Credo, G.M., et al., "External quantum efficiency of single porous silicon nanoparticles," *Applied Physics Letters*, vol. 74, No. 14, pp. 1978-1980. Apr. 5, 1999.

Mason, et al., "Luminescence of Individual Porous Si Chromophores," *Physical Review Letters*, vol. 80, No. 24, pp. 5405-5408. Jun. 15, 1998.

Singh, et al., "Quenching and recovery of photoluminescence intensity of silicon nanoparticles embedded in optically transparent polymers," *Semicond. Sci. Technol.*, vol. 17, No. 10, pp. 1123-1127. Sep. 20, 2002.

Tsuo, et al., "Environmentally Benign Silicon Solar Cell Manufacturing," Presented at the $2^{nd}$ World Conference and Exhibition on Photovoltaic Solar Energy Conversion, Jul. 6-10, 1998. Vienna, Austria. (7 pages).

International Searching Authority: Notification of Transmittal of the International Search Report and the Written Opinion of the International Searching Authority for International Application No. PCT/US 06/31230, mailed Sep. 15, 2008 (10 pages).

\* cited by examiner

REMOTE IDENTIFICATION OF EXPLOSIVES AND OTHER HARMFUL MATERIALS

CROSS REFERENCE TO RELATED APPLICATIONS

The present application claims the benefit of U.S. Provisional Patent Application 60/400,784 filed Aug. 2, 2002.

TECHNICAL FIELD

The present invention relates in general to chemical detection and sensing, and in particular, to exploiting the photoluminescence properties of nanometer-size particles for chemical and hazardous materials detection.

BACKGROUND INFORMATION

"Markers" or "taggants" are terms used to represent any material that can be added to explosives, chemical weapons, etc. in order to assist in identifying the explosive/weapon or its source before, after, or both before and after its detonation or use. While the motive for including such markers or taggants in explosives and other weapons is clearly anti-terrorism, taggants have also been proposed as anti-counterfeiting devices, anti-tampering devices, and as quality control devices in commercial products ranging from gasoline to perfumes ("Black and Smokeless Powders: Technologies for Finding Bombs and the Bomb Makers," Committee on Smokeless and Black Powder, National Research Council, 1998).

While such markers or taggants can aid authorities in their investigation of detonated explosives or deployed chemical weapons and in identifying the source of such seized weapons, they generally cannot prevent the harmful agent from being used. Furthermore, the taggants must be inserted during the production of the harmful agent. This means that weapons or other harmful devices fabricated by terrorist elements or rogue nations would likely be unidentifiable.

One way of overcoming the above-mentioned limitations is to devise strategies for chemically sensing explosives, chemical weapons, and other harmful agents by exploiting the high vapor pressures that many of them possess and the emission of nitrogen- and phosphorus-containing free radicals from the explosives, chemical weapons, and other harmful agents. This is the case for phosphorus-containing chemical nerve agents like sarin, soman, tabun, and VX and for nitro-containing explosives like trinitrotoluene (TNT) and nitroglycerine. Chemical sensing, such as utilizing spectral characteristics, could be used to detect such harmful materials in public places like airports, subways, shopping malls, etc. This would allow for the pre-emptive identification of harmful materials, before they have inflicted any damage.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
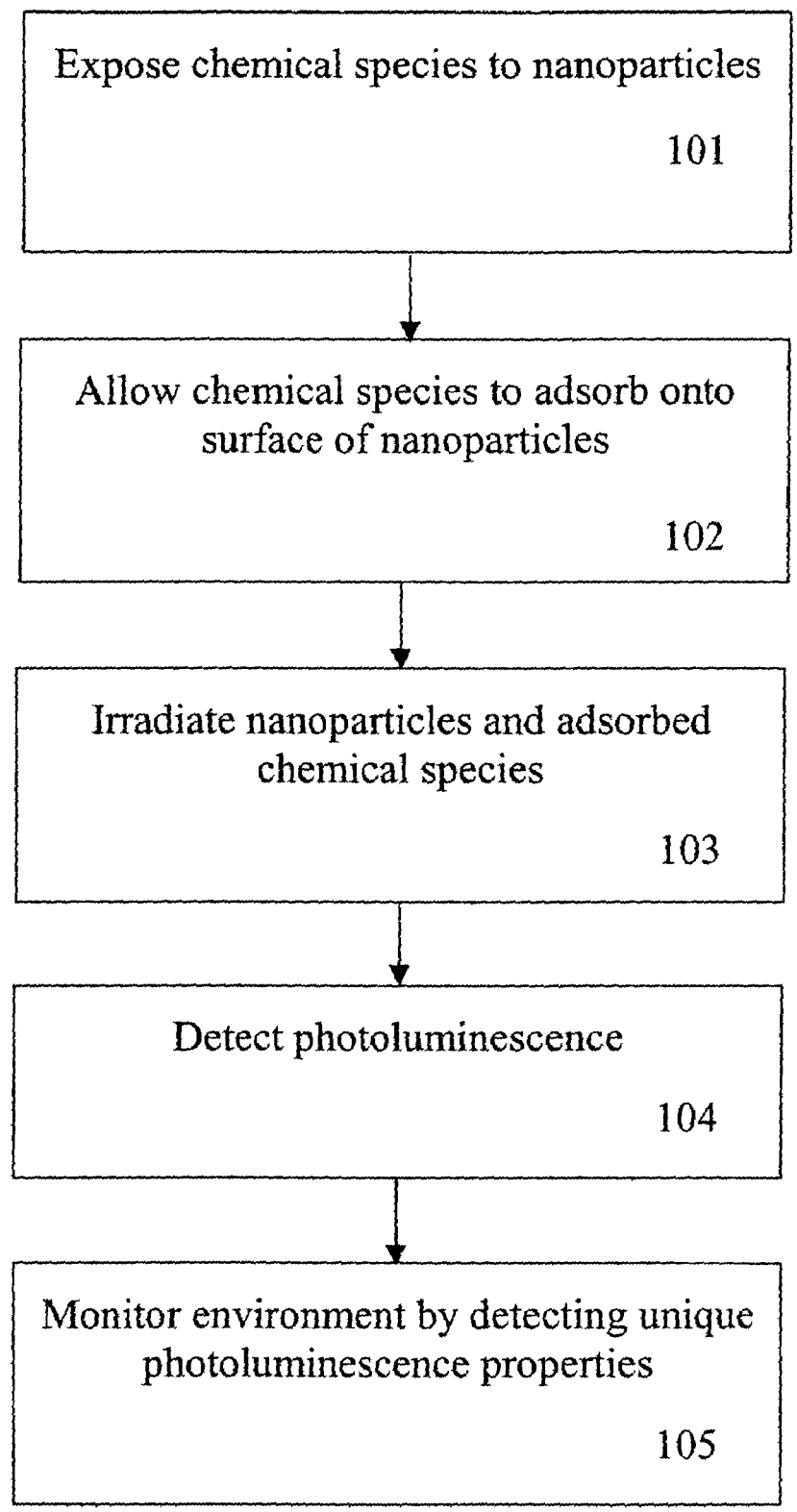
FIG. 1 illustrates, in general terms, a process of using nanoparticles for chemical sensing.

For semiconductors, electronic excitations take the form of electron-hole pairs called excitons. Quantum confinement is a phenomenon which occurs when a semiconductor particle's size is decreased below its excitonic Bohr radius, which is generally in the 10 to 50 nanometer (nm) range, but is different for each material. If one imagines a shrinking semiconductor particle, at the quantum confinement threshold, the semiconductor's bandgap begins to increase. As the particle continues to get smaller, the bandgap continues to increase, but the valance and conduction bands begin to separate into discreet energy levels reminiscent of molecular orbitals.

In addition to an increased bandgap, quantum-confined particles, or "quantum dots," possess interesting photoluminescent behavior as well. This is due to the fact that electronic transitions previously unallowed in the bulk state, may suddenly become allowed in the quantum confined state. By careful control of the particle size, the bandgap and photoluminescence (PL) properties can be tuned to yield materials with unique optical properties and spectral characteristics.

The present invention comprises a process of using nanometer-size particles (also known as nanoparticles or nanocrystals, according to the present invention), in the sensing and identification of chemicals and harmful agents by exposing such chemicals and harmful agents to the nanoparticles. Such exposure could be in the gas phase, the liquid phase, or the solid phase, and could include mixed phase exposures. Such sensing would exploit unique properties of the nanoparticles, specifically unique photoluminescence properties of the nanoparticles.

Nanoparticles, according to the present invention, are particles comprising finite bandgap materials, and having particle diameters which are generally less than about 100 nm. Finite bandgap materials, in contrast to zero bandgap and infinite bandgap materials, can be categorized as semimetals, semiconductors, insulators, and combinations thereof. Examples of finite bandgap materials include, but are not limited to, silicon (Si), gallium arsenide (GaAs), cadmium sulfide (CdS), cadmium selenide (CdSe), titanium dioxide ($TiO_2$), diamond, cerium oxide ($CeO_2$), silicon oxide ($SiO_2$), aluminum oxide ($Al_2O_3$), and the like and combinations thereof.

Photoluminescence (PL), according to the present invention, comprises all forms of luminescence including fluorescence, phosphorescence, and combinations thereof. The excitation radiation, which induces photoluminescence, is typically in the ultraviolet (UV) region of the electromagnetic (EM) spectrum, but can generally be in any or all regions of the electromagnetic spectrum capable of inducing photoluminescence in the nanoparticles. Photoluminescence, according to the present invention, is typically in the visible (optical) region of the electromagnetic spectrum, but can generally be in any or all regions of the electromagnetic spectrum.

Photoluminescence of the nanoparticles, according to a process of the present invention, is induced when the nanoparticles are irradiated with light, particularly with wavelengths found in the UV region of the electromagnetic spectrum. The emitted radiation (the photoluminescence) is generally in the visible (optical) region of the electromagnetic spectrum. When a chemical species adsorbs onto the surfaces of the nanoparticles, the photoluminescence properties of the nanoparticles are altered. Chemical sensing is accomplished by detecting and, in some embodiments, analyzing the altered photoluminescence properties. Sensing, according to the present invention, includes, but is not limited to, detecting, analyzing, monitoring, and the like and combinations thereof.

In some embodiments of the present invention, the nanoparticles comprise quantum confined particles, wherein the bandgap of said quantum confined particles has been increased (in terms of energy) relative to the bulk material.

In some embodiments of the present invention, the nanoparticles are chemically functionalized prior to their use in chemical sensing. Such functionalization broadens the range in which the nanoparticles' photoluminescence properties can be tuned, and it can vary the efficiency with which chemical species can be adsorbed onto the nanoparticle surface.

In some embodiments of the present invention, the nanoparticles comprise silicon nanoparticles.

Nanoparticles, according to a process of the present invention, can be made by any known technique which suitably provides particles which reliably photoluminescence in the manner described herein. Such nanoparticles range generally in size from about 1 nm to about 100 nm, specifically from about 1 nm to about 50 nm, and more specifically from about 1 nm to about 10 nm. For any given application utilizing a quantity of nanoparticles, such nanoparticles have a size variation of generally up to about 20 nm, specifically up to about 10 nm, and more specifically up to about 3 nm.

In general terms, a process of the present invention comprises of a number of steps. Referring to FIG. 1, nanoparticles (e.g., silicon nanoparticles) of a specific particle size and/or range of sizes having initial photoluminescence properties are exposed to a chemical species of interest in a controlled environment 101 (e.g., 25° C., 1 atm of $N_2$). For example, the initial photoluminescence properties can be the photoluminescence properties that the nanoparticles exhibit when initially produced. Also, for example, the initial photoluminescence properties can be the photoluminescence properties that the nanoparticles exhibit after initial production, any further processing (such as, but not limited to, combining the nanoparticles with a dispersant or the like such as an aerosol) and exposure to a controlled environment, but before contact with a chemical species of interest in the controlled environment. Exposure occurs such that the chemical species of interest adsorbs onto the surface of the nanoparticles 102. The nanoparticles with the adsorbate present are irradiated with radiation (e.g., UV light) of a given frequency or frequencies 103. Emitted radiation (photoluminescence) is then detected and analyzed 104 with a device, such as, but not limited to, a spectrometer, to determine how the photoluminescence properties of the nanoparticles have been altered (e.g., shifted) relative to the initial photoluminescence properties of the nanoparticles in the same environment but with the absence of the particular chemical species of interest to provide for a pre-defined altered photoluminescence property or properties that corresponds to the particular chemical species of interest. The chemical species of interest can then be detected in an environmental setting by monitoring for altered photoluminescence properties and comparing the altered photoluminescence properties to the pre-defined altered photoluminescence properties 105. Thus, an environment can be monitored for a particular species of interest by looking for a particular change (i.e., monitoring for a specific frequency or frequencies) in the photoluminescence behavior of the nanoparticles and comparing to the pre-defined altered photoluminescence properties.

Exposing, as referred to herein, comprises any time period, temperature, pressure, and atmosphere that suitably provides for the chemical species of interest to adsorb onto the surface of the nanoparticles according to a process of the present invention as described herein. Exposing generally includes a temperature generally in the range of from about −20° C. to about +200° C., a pressure generally in the range of from about 1 millitorr to about $1 \times 10^5$ torr, a time period generally in the range of from about 1 millisecond to about 10 hours, and a controlled atmosphere. A controlled atmosphere includes, but is not limited to, nitrogen, hydrogen, argon, oxygen, air, fluorocarbons, chlorofluorocarbons, helium, and the like and combinations thereof.

In some embodiments of the present invention, the steps outlined above are carried out for a number of chemical species of interest, thereby creating a database of photoluminescence shifts, and increasing the number of chemical species which can be detected. Sensing, according to the present invention, can thus determine the presence and identity of one or more unknown chemical species.

In some embodiments of the present invention, the adsorption of a chemical species of interest onto the surfaces of the nanoparticles is a reversible process. In other embodiments, the adsorption is essentially non-reversible. Adsorption, according to the present invention, includes, but is not limited to, physisorption, chemisorption, and combinations thereof.

In some embodiments of the present invention, a controlled environment comprises a self-contained box or room.

In some embodiments of the present invention, irradiation of the nanoparticles with UV radiation is done with a UV laser.

In some embodiments of the present invention, the photoluminescence is detected and/or analyzed by an optical detection method. Optical detection methods include, but are not limited to, wavelength selective detectors.

In some embodiments of the present invention, the photoluminescence is detected and/or analyzed by a spectrometer. In other embodiments, optical filters are employed.

In some embodiments of the present invention, an optical amplifying device (e.g., a photomultiplier tube) is used to increase the sensitivity of the sensing by several orders of magnitude.

In some embodiments of the present invention, the concentration of the chemical species of interest can be determined and/or monitored. These embodiments rely on a calibration of the photoluminescence change in the nanoparticles with known chemicals of known concentration.

In some embodiments of the present invention, the chemical species of interest (the object of the sensing) is a harmful agent. Harmful agents, according to the present invention, include, but are not limited to, toxins, carcinogens, mutagens, lachrymators, flammable species, nerve agents, explosives, and the like and combinations thereof.

In some embodiments of the present invention, the decomposition products of the actual species of interest are being sensed, such as detecting explosives, chemical weapons, and other harmful agents. Such species often contain nitrate and phosphate moieties. Slow decomposition results in nitrogen- and phosphorus-containing free radicals being emitted. These products of decomposition can, at times, be more easily detected by the present invention than the actual species of interest.

In an embodiment of the present invention, harmful materials would be detected by spraying a suspect item (e.g., luggage or mail) with an aerosol of nanoparticles (e.g., silicon nanoparticles) having one or more pre-defined altered photoluminescence properties, illuminating the suspect item with a UV laser in the process of spraying it with the aerosol of nanoparticles, measuring the photoluminescence shift or change, i.e., measuring the altered photoluminescence properties, and observing whether or not there is a pre-defined shift or change in the photoluminescence spectra corresponding to a known—and already evaluated—chemical agent (sarin, for example), i.e., comparing the altered photoluminescence properties to the one or more pre-defined altered photoluminescence properties. Such a process could be carried out remotely from a distance. In the case of sarin, the high vapor pressure of this nerve agent might render the environment in the immediate vicinity of the article to be relatively high in sarin content—even if it were enclosed in some type of crude container that permitted the escape of merely trace amounts. The sarin vapor would then cause a predetermined shift or change in the photoluminescence spectra of the nanoparticles on account of the altered chemical environment. A variation on this embodiment would be to use the nanoparticle aerosol in the vicinity of a military weapons depot, whereby leaks in containers containing explosives and chemical weapons could be detected and identified.

Another embodiment of the present invention would comprise flooding a room (or a public place where there are people present) with nanoparticles of the present invention, exposing such nanoparticles to UV radiation, and monitoring their photoluminescence properties. In such an embodiment, care must be taken to ensure that the nanoparticles are non-toxic. In the event that an explosive or chemical agent was introduced into the room, a pre-defined shift or change in the photoluminescence spectrum of the nanoparticles would be observed corresponding to the particular harmful agent introduced into the room, e.g., the nanoparticles would exhibit altered photoluminescence properties that could be compared to one or more pre-defined altered photoluminescence properties. Identification of harmful agents in such a manner would likely permit their containment before they caused devastating effects.

Variations on the above-mentioned embodiments would be the detection of residues of harmful agents on the clothing or hands of individuals. Thus, an individual who merely came into contact with such agent could be identified.

Identification of agents as described herein need not be limited to screening techniques, however. By a having pre-defined knowledge of how a particular harmful agent alters the chemical environment of the nanoparticles and alters the photoluminescence properties of the nanoparticles (and how it shifts the corresponding photoluminescence spectrum), it is possible to use solutions of these nanoparticles in forensic laboratories to identify harmful agents.

Another embodiment of the present invention would include using nanoparticles of the present invention as traditional markers or taggants in explosives, chemical weapons, and other harmful agents. Since the taggants must possess some unique property (e.g., radioactivity, isotopic abundance, etc.), the unique photoluminescence properties of the nanoparticles should be suitable for such a role. While this embodiment may not permit pre-emptive detection of such agents, nanoparticles may prove superior to traditional taggants, especially in that their optical properties can be tuned by slight variations in their size. Other variations of this embodiment would include the use of nanoparticles as taggants for anti-counterfeiting, anti-tampering, and anti-piracy purposes. Thus, their inclusion in currency, books, software, music CDs, etc. is envisioned. Because their optical properties are tunable, they may be more difficult for unauthorized parties to replicate and counterfeit.

Although the present invention has been described with respect to specific embodiments, the details thereof are not to be construed as a limitation, for it will be apparent to those of skill in the art that various embodiments, changes and modifications may be resorted to without departing from the spirit and scope thereof, and it is understood that such equivalent embodiments are intended to be included within the scope of the present invention.

What is claimed is:

1. A process comprising:
    a) exposing a chemical species to nanoparticles such that said chemical species physisorbs onto a surface of the nanoparticles as an adsorbate, wherein such exposing is carried out as an exposure selected from the group consisting of a gas phase exposure, a solid phase exposure, and combinations thereof;
    b) irradiating the nanoparticles comprising the adsorbate with radiation;
    c) detecting altered photoluminescence properties of the nanoparticles comprising the adsorbate as a result of the chemical species being physisorbed onto the surface of the nanoparticles; and
    d) analyzing the altered photoluminescence properties by comparing to one or more pre-defined altered photoluminescence properties, to provide for an identifying of the chemical species.

2. The process of claim 1, wherein the radiation comprises ultraviolet radiation.

3. The process of claim 1, wherein the nanoparticles comprise quantum confined nanoparticles.

4. The process of claim 1, wherein the nanoparticles comprise silicon nanoparticles.

5. The process of claim 1, wherein the one or more pre-defined altered photoluminescence properties are provided by exposing nanoparticles having initial photoluminescence properties to one or more known chemical species.

6. The process of claim 1, wherein the chemical species is selected from the group consisting of toxins, carcinogens, mutagens, lachrymators, flammable species, nerve agents, explosives, and combinations thereof.

7. The process of claim 1, wherein the adsorption of a chemical species onto the surface of the nanoparticles comprises a reversible process.

8. The process of claim 1, wherein the nanoparticles range in size from about 1 nm to about 100 nm.

9. The process of claim 1, wherein the nanoparticles are present in an aerosol.

10. The process of claim 1, wherein the detecting the altered photoluminescence properties comprises utilizing a wavelength selective detector.

11. The process of claim 1, wherein the analyzing the altered photoluminescence properties comprises utilizing a wavelength selective detector.

12. The process of claim 1, wherein the detecting and analyzing the altered photoluminescence properties comprises utilizing a spectrometer.

13. The process of claim 1, wherein the detecting and analyzing the altered photoluminescence properties comprises utilizing an optical filter.

14. The process of claim 1, wherein the nanoparticles are silicon nanocrystals.

15. The process of claim 1, further comprising determining a concentration of the chemical species.

16. A process comprising:
    a) exposing a chemical species to quantum-confined silicon nanoparticles such that said chemical species physisorbs onto a surface of the quantum-confined silicon nanoparticles as an adsorbate, wherein such exposing is carried out as an exposure selected from the group consisting of a gas phase exposure, a solid phase exposure, and combinations thereof
    b) irradiating the quantum-confined silicon nanoparticles comprising the adsorbate with ultraviolet radiation;
    c) detecting altered photoluminescence properties of the quantum-confined silicon nanoparticles comprising the adsorbate as a result of the chemical species being physisorbed onto the surface of the quantum-confined silicon nanoparticles; and d) analyzing the altered photoluminescence properties by comparing to one or more pre-defined altered photoluminescence properties, to provide for an identifying of the chemical species.

17. The process of claim 16, wherein the one or more pre-defined altered photoluminescence properties are provided by exposing quantum-confined silicon nanoparticles having initial photoluminescence properties to one or more known chemical species.

18. The process of claim 16, wherein the chemical species is selected from the group consisting of toxins, carcinogens, mutagens, lachrymators, flammable species, nerve agents, explosives, and combinations thereof 19. The process of claim 16, wherein the adsorption of a chemical species onto a surface of the quantum-confined silicon nanoparticles comprises a reversible process.

20. The process of claim 16, wherein the detecting the altered photoluminescence properties comprises utilizing a wavelength selective detector.

21. The process of claim 16, wherein the analyzing the altered photoluminescence properties comprises utilizing a wavelength selective detector.

22. The process of claim 16, wherein the detecting and analyzing the altered photoluminescence properties comprises utilizing a spectrometer.

23. The process of claim 16, wherein the detecting and analyzing the altered photoluminescence properties comprises utilizing an optical filter.

24. The process of claim 16, further comprising determining a concentration of the chemical species.

25. The process of claim 16, wherein the step of exposing is carried out in the gas phase.

* * * * *